US008597641B2

(12) United States Patent
Harz et al.

(10) Patent No.: US 8,597,641 B2
(45) Date of Patent: *Dec. 3, 2013

(54) INSTANT ENZYME FORMULATIONS FOR ANIMAL NUTRITION

(75) Inventors: Hans-Peter Harz, Dudenhofen (DE); Roland Betz, Niederkirchen (DE); Wolfgang Heinzl, Wachenheim (DE); Günter Gaus, Biblis (DE)

(73) Assignee: BASF SE, Lugwigshafen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 12/748,604

(22) Filed: Mar. 29, 2010

(65) Prior Publication Data

US 2010/0247507 A1 Sep. 30, 2010

Related U.S. Application Data

(63) Continuation of application No. 09/959,985, filed as application No. PCT/EP00/04475 on May 17, 2000.

(30) Foreign Application Priority Data

May 18, 1999 (DE) .................................. 199 22 753

(51) Int. Cl.
*A61K 38/43* (2006.01)
*A61K 38/54* (2006.01)
*C12N 11/00* (2006.01)
*C12N 11/16* (2006.01)
*C12N 11/02* (2006.01)

(52) U.S. Cl.
USPC .......... 424/94.3; 424/94.1; 435/174; 435/177

(58) Field of Classification Search
USPC ........................ 424/94.1, 94.3; 435/174, 177
See application file for complete search history.

(56) References Cited

U.S. PATENT DOCUMENTS

| 3,594,325 | A |   | 7/1971  | Feierstein et al. |         |
|-----------|---|---|---------|-------------------|---------|
| 3,687,853 | A |   | 8/1972  | Natali et al.     |         |
| 4,016,040 | A |   | 4/1977  | Win et al.        |         |
| 4,731,249 | A | * | 3/1988  | Findley           | 426/69  |
| 4,820,627 | A |   | 4/1989  | McGeehan          |         |
| 4,933,192 | A |   | 6/1990  | Darling et al.    |         |
| 5,100,509 | A |   | 3/1992  | Pisecky et al.    |         |
| 5,236,503 | A |   | 8/1993  | Jones             |         |
| 5,318,903 | A |   | 6/1994  | Bewert et al.     |         |
| 5,622,710 | A |   | 4/1997  | Binder et al.     |         |
| 5,700,497 | A |   | 12/1997 | Stone et al.      |         |
| 5,763,157 | A |   | 6/1998  | Treml et al.      |         |
| 5,814,501 | A | * | 9/1998  | Becker et al.     | 435/174 |
| 5,827,709 | A | * | 10/1998 | Barendse et al.   | 435/188 |
| 5,871,802 | A |   | 2/1999  | Gao et al.        |         |
| 5,972,669 | A | * | 10/1999 | Harz et al.       | 435/188 |
| 7,556,802 | B1|   | 7/2009  | Harz et al.       |         |
| 7,611,701 | B2| * | 11/2009 | Barendse et al.   | 424/94.6|
| 2003/0054511 | A1 |   | 3/2003 | Andela et al.    |         |

FOREIGN PATENT DOCUMENTS

| DE | 41 19 281 A1 | 12/1992 |
|----|--------------|---------|
| EP | 0758018 A1   | 2/1997  |
| GB | 2 186 796 A  | 8/1987  |
| JP | 55-051429 A  | 4/1980  |
| JP | 61-257229 A  | 11/1986 |
| JP | 62-272945 A  | 11/1987 |
| JP | 01-067239 A  | 3/1989  |
| JP | 04-151243 A  | 5/1992  |
| JP | 06-505881 T  | 7/1994  |
| JP | 06-296460 A  | 10/1994 |
| WO | WO-93/14645 A1 | 8/1993 |
| WO | WO-97/12958 A2 | 4/1997 |
| WO | WO-98/28409 A1 | 7/1998 |
| WO | WO-98/55599 A2 | 12/1998 |
| WO | WO-99/32612 A1 | 7/1999 |

OTHER PUBLICATIONS thefreedictionary.com, "agglomerate", http://www.thefreedictionary.com/p/agglomerate, accessed Apr. 2, 2012.*
Glatt, "Fluid Bed Systems", Product Data Sheet found at http://www.cjtech.co.kr/x%20laboratory%20unit_e.pdf, accessed on Jan. 15, 2009.
International Starch Institute, "Sieve Table", 1999, http://www.starch.dk/isi/tables/screens.htm.
Garthe, J.W., "The Chemical Composition of Degradable Plastics", Agricultural and Biological Engineering, (1994), 4 pages.
Refstrup, E., "Recent Advances in Agglomeration during Spray Drying", Translation of Reprint No. S-351 from Zeitschrift für Lebensmitteltechnologie (ZFL), Oct. 1992.

* cited by examiner

*Primary Examiner* — Thane Underdahl
(74) *Attorney, Agent, or Firm* — Novak Druce Connolly Bove + Quigg LLP (57) ABSTRACT

The invention relates to a process for preparing an instant enzyme formulation; instant enzyme formulations obtainable by this process and feedstuff compositions prepared using instant enzyme formulations of the invention.

41 Claims, 4 Drawing Sheets

INSTANT ENZYME FORMULATIONS FOR ANIMAL NUTRITION

RELATED APPLICATIONS

This application is a continuation of U.S. application Ser. No. 09/959,985, filed Nov. 14, 2001, which is a national stage application (under 35 U.S.C. §371) of PCT/EP2000/04475 filed May 17, 2000, which claims benefit of German Application No. 199 22 753.5, filed May 18, 1999. The entire contents of each of these applications are hereby incorporated by reference herein.

FIELD OF THE INVENTION

The present invention relates to novel instant enzyme formulations, processes for their preparation and to their use for animal nutrition.

BACKGROUND OF THE INVENTION

Enzymes are widely used in animal nutrition, with the purpose of increasing the bioavailability of certain nutrients or improving the feed conversion efficiency. Thus, for example, the enzyme phytase is used to release the phosphorus bound in phytate and thus ensure its bioavailability. It is further known to add NSP (nonstarch polysaccaride) enzymes to the feed in order, inter alia, to reduce the viscosity of the feed in the alimentary tract and thus improve the conversion efficiency of the feed.

However, feedstuffs containing an added enzyme preparation are frequently pelleted, expanded or extruded, as a result of which, owing to the resultant relatively high temperatures, the enzyme activity is reduced or completely destroyed. To avoid this disadvantage, enzymes in the form of liquid formulations are sprayed onto the already-pelleted feedstuff.

However, the use of liquid enzyme preparations also has disadvantages. Owing to the high water content or the high water activity, enzyme formulations of this type can be stabilized only with great difficulty. Frequently, a sharp drop in activity, an increase in microbial count and an impairment of the appearance of the preparation is observed during storage. In particular, owing to temperature fluctuations, precipitation of the enzymes or other proteins present therein may frequently be observed. In addition to the inadequate keeping quality, moreover, the low activity per unit volume is a serious disadvantage with liquid formulations.

WO 97/12958 discloses enzyme-containing microgranules which are obtained by agglomeration. They comprise an enzyme preparation applied to a support and at least one binder or decomposition accelerator. The granules are, in addition, polymer-coated and have a particle size of less than 0.4 mm. The enzyme content for a typical composition is less than 40% by weight. The preparation of an instant enzyme formulation which is suitable, in particular, as an easily handled feed additive is not described therein.

It is an object of the present invention therefore to provide an improved enzyme formulation which avoids the above-described disadvantages of liquid formulations.

DESCRIPTION OF THE INVENTION

In particular, enzyme formulations are to be prepared which have a high enzyme content and in particular a high enzyme activity per unit volume, are stable in storage and can be applied to feedstuffs in a simple manner.

We have found that this object is achieved, surprisingly, by providing solid instant enzyme formulations.

The instant enzyme powders of the invention have a number of critical advantages:

At the user's premises, they can rapidly be converted into a liquid formulation owing to their high solubility or dispersibility in an aqueous medium. The excellent instant properties guarantee rapid dissolution without any particular technical complexity. After their dissolution in a liquid medium, such as water, an aqueous solution or dispersion, the preparations of the invention can be applied conventionally to the feedstuff. Since the enzyme preparations of the invention occur in agglomerated form, they can be handled particularly easily. In particular they have an excellent free-flowing quality, are virtually dust-free and have no tendency to lump formation during dissolution. However, it is of particular importance that, compared with liquid preparations, they have a markedly improved keeping quality. In addition, they have a relatively high enzymatic activity per unit volume, which minimizes storage and transport costs.

The instant enzyme formulations of the invention are prepared by agglomeration in a novel manner.

The invention thus firstly relates to a process for preparing a dry granulated instant enzyme formulation which comprises a) introducing a pulverulent material which is selected from
   i) an inorganic or organic support which is soluble or dispersible, preferably soluble, in aqueous medium;
   ii) an enzyme preparation which is soluble in aqueous medium; and
   iii) mixtures of i) or ii);
and b) agglomerating the pulverulent material by simultaneous or time-staggered spraying of one or more spray media to form an instant powder, preferably in a fluidized bed, the spray media being selected from enzyme solutions, binder solutions, binder dispersions and binder-containing enzyme solutions, with the proviso that spraying comprises the application of at least one enzyme-containing solution if the pulverulent material introduced does not comprise an enzyme preparation.

The process of the invention can be carried out either continuously or batchwise.

A first preferred variant of the process of the invention relates to the batchwise preparation of an instant powder:

Agglomeration is performed batchwise in the fluidized bed using a pulverulent material in accordance with the above definition. In this case this powder, in particular a pulverulent inorganic or organic support which is soluble or dispersible in aqueous medium, is introduced into a fluidized bed. The fluidization is performed, for example, by feeding preheated air. An enzyme-containing solution is sprayed into the fluidized bed, as a result of which the powder is wetted by this solution and is increasingly agglomerated due to the adhesive properties of the solution. The solution can be sprayed into the fluidized bed from the top (top spray process) or from the bottom (bottom spray process). When the desired agglomerate size is achieved, or the desired enzyme activity or amount is set, the product is discharged from the dryer and classified, for example using a screen.

To obtain the highest possible activity in the instant powder, in the batch procedure the introduction of support should be kept as small as possible and the fluidized bed at the end of the process should be operated as far as possible up to the maximum bed height. The specific mode of operation of the fluidized bed depends on the respective bed height. With increasing bed height during the process, the air flow rate and spraying rate also increase. At the beginning of the process, preferably, a minimum amount of introduced material should be ensured, since otherwise problems can occur, for example due to sticking and lump formation in the product. The individual process parameters must be carefully adapted to the respective bed height in the fluidized bed during the process period. If the mode of operation is too dry, too little agglomeration takes place, and if the mode of operation is too moist, the product sticks together intensively, which results in lump formation and sticking to the apparatus.

The material introduced into the fluidized bed can alternatively be a dry pulverulent enzyme preparation. If a pulverulent enzyme preparation is introduced, preferably a pulverulent enzyme preparation obtained by spray-drying is used, which preparation if appropriate is preagglomerated before the enzyme solution is sprayed.

The spray-drying of liquid enzyme preparations can be carried out in a conventional manner. For this purpose the enzyme solution is pumped to the atomizer in the spraying tower. The atomization is performed, for example, by means of a pressure nozzle (single-component nozzle), a two-component nozzle or a centrifugal atomizer The droplets are dried by a hot air stream passed into the spray-dryer. When centrifugal atomizers are used, drying is preferably performed in concurrent flow. In the case of nozzles, the drying can also be performed in countercurrent flow or mixed flow. The powder can be discharged at the tower or it is entrained by the air stream and separated off in a cyclone and/or filter. Depending on the product and mode of operation, post-drying may be necessary, which can be performed in an internal fluidized bed flanged onto the spray-dryer or in an external fluidized bed.

A further preferred variant of the process according to the invention relates to the continuous fluidized-bed agglomeration without using an inorganic or organic support by continuous spraying of an enzyme solution. For this purpose, in a fluidized-bed dryer, at the start of the process a pulverulent material, for example enzyme powder obtained by spray-drying, is introduced. It is fluidized, for example, by feeding preheated air. An enzyme-containing solution is sprayed onto the fluidized bed as a result of which the powder introduced is wetted by this solution and increasingly agglomerated by its adhesive properties. Simultaneously, a partial amount of agglomerate is discharged from the fluidized bed continuously or semi-continuously, i.e. times at intervals. The amount of agglomerate discharged corresponds roughly to the amount of enzyme fed via the spray nozzle, corrected by the different contents of solvent in the spraying solution and in the agglomerate. In this mode of operation, therefore, material must only be introduced once during the startup of the process. The discharge is classified, for example using a screen. Coarse material arising during this operation can be ground and continuously recirculated back into the fluidized bed. Fines fractions, for example from the exhaust air filter unit, can also be continuously recirculated.

According to a further process variant, the agglomerate of the invention is prepared continuously, more precisely with continuous feed of a dry pulverulent introduced material, for example an organic or inorganic support or an enzyme powder, into the fluidized-bed dryer.

Suitable dryers for this are particularly fluidized-bed dryers having a plurality of spraying zones and if appropriate drying zones. In the first zone, support or dry enzyme powder is fed and fluidized, and enzyme solution and/or binder is sprayed in. The agglomerate formed in this zone is transferred to the next zone. Into this zone and possibly into one or more further zones, enzyme solution and/or binder solution of the same or different composition can also be sprayed in. The water is taken off from the sprayed enzyme solution or binder solution by a feed air stream common to all zones or by separate feed air streams which are appropriately heated. In one or more of the last zones post-drying can further be carried out. Product discharge also takes place here. The product is worked up as described above.

A further preferred process variant comprises spray-drying of enzyme solution coupled with the subsequent agglomeration of the spray-dried enzyme powder. This can be carried out batchwise or continuously. The continuous procedure is preferred.

Processes of this type can be carried out using conventional spray-drying systems. Advantageously, however, it is carried out in apparatuses which are known as FSD (fluidized spray dryer), SBD (spray bed dryer) or MSD (multistage dryer).

It is advantageous in this process variant if relatively large particles are produced by spray-drying (mean diameter >80 µm). The resultant fines fraction of the powder can be reincorporated into the process right in the spray dryer, if this fines fraction, for example after separation in a cyclone or filter, is recirculated back into the moist zone of the dryer. The actual agglomeration then takes place in a further stage in a fluidized bed. This stage can be integrated into the spray dryer (internal fluidized bed) or it can be carried out in a separate apparatus (additional fluidized bed). An enzyme solution, an enzyme solution which additionally comprises binder or only binder in dissolved or dispersed form is injected into the fluidized bed with simultaneous drying. The powder prepared by the spray-drying comprises an enzyme which is preferably identical to the sprayed enzyme. The composition and amount of the injected liquids depend on the adhesive properties of the solution sprayed in, the agglomerate size to be achieved and the process conditions. Based on the powder to be agglomerated, the amount of spraying solution, i.e. the amount of injected liquid, can be from about 10 to 200%. Depending on the amount sprayed, a post-drying in a further stage may be necessary. The product is then worked up in the manner described above.

Further preferred process parameters of the process according to the invention:

Owing to the generally high temperature lability of the sprayed enzymes, controlling the product temperature is of particular importance during the process of the invention. It should be chosen to be as low as possible, since with increasing temperature and/or duration of the spray-drying process and agglomeration process the losses of activity increase. Typically, the product temperature on spray-drying, i.e. the temperature of the solid spray-dried powder, is from about 50 to 75° C., in particular less than about 70° C., frequently less than 60° C. The longer the residence time in the fluidized bed, the lower the temperature which should be selected.

The product temperature during the agglomeration and drying in the fluidized bed, i.e. the temperature of the agglomerate situated in the fluidized bed, must be chosen to be low because of the relatively long residence time in the apparatus and is from about 30 to 50° C., in particular less than 45° C. and preferably less than 40° C.

To decrease the residual moisture content further, carrying out a post-drying step is preferred. During the post-drying, the product temperature should also be in the abovementioned range and in particular be 50° C. or below. The post-drying decreases the residual moisture content in the preparations according to the invention to values of less than about 15% by weight, preferably about 2 to 10% by weight.

The drying during the agglomeration or the post-drying is achieved by using preheated feed air. The feed air temperature, which can differ according to the selected preset product temperature, air flow rate and spraying rate, is generally in a range from 30 to 80° C. The post-drying is performed at a lower temperature, that is to say in a range from about 35 to 55° C.

The agglomeration time is likewise dependent on the size of the batch chosen but is roughly in the range of one or more hours.

To further improve the product quality it can be advantageous to provide the resultant agglomerate with a water-soluble coating. This largely prevents the formation of abraded product and thus dust formation. Owing to the allergenic potential of some enzymes, such a measure is of particular interest. Examples of suitable coating materials are the above-described binders, for example hydroxypropylmethylcellulose and polyvinylpyrrolidone, or polyethylene glycols and block polymers of polyoxyethylene and polyoxypropylene. The coating process can be carried out, for example, in a fluidized bed, in particular if, to apply the coating, a solution or suspension of the coating materials, for example the above-mentioned materials, is used. The solutions or dispersions used have a coating medium content in the range from about 5 to 50% by weight, based on the total weight of the solution or dispersion. If melts are used, for example melts of PEG (polyethylene glycol) or block polymers of polyoxyethylene and polyoxypropylene, it is expedient to carry out the coating step in a fluidized bed or a mixer, for example a plowshare mixer from Lödige.

After the coating has been applied, renewed drying may be necessary. In this case also the product temperature should be in the range from about 30 to 50° C.

The content by weight of coating material in the end product is from about 5 to 20%, based on the total weight of the instant formulation.

The introduced material used according to the invention for the agglomeration is preferably selected from inert inorganic water-soluble or water-dispersible powders, pulverulent, water-soluble or water-dispersible organic polymers or pulverulent preferably water-soluble enzyme preparations. An "inert" support or an "inert" introduced material must not exhibit any adverse interactions with the enzyme(s) of the instant formulation, for example cause an irreversible inhibition of enzyme activity, and must be safe for use as a processing aid in a feedstuff additive. In addition, it must possess a particle size distribution suitable for the fluidized-bed granulation. The mean particle size (mean diameter) is from about 30 to 300 μm, preferably from about 50 to 200 μm. In principle, agglomerization is also possible using larger particles; however, this leads to the formation of larger agglomerates having a longer dissolution time.

Examples of suitable low-molecular inorganic supports or introduced materials are sodium chloride, calcium carbonate, sodium sulfate and magnesium sulfate. Examples of suitable organic powders are, in particular, sugars, for example glucose, fructose, sucrose, and dextrins and starch degradation products. Examples of organic polymer supports are, in particular, starch and cellulose preparations, in particular corn starch.

The enzyme solution used according to the invention for spray-drying or agglomeration comprises at least one enzyme which can be used as a feedstuff additive dissolved in an aqueous phase, for example sterile demineralized water. The solution has a protein content in the range of from about 1 to 50% by weight, preferably from about 10 to 35% by weight, based on the total weight of the solution. The pH is generally in the range from about 4 to 9. The solution can comprise other customary additives. Examples are: buffers, for example phosphate buffer; enzyme stabilizers, for example alkali metal salts or alkaline earth metal salts, such as sodium sulfate or magnesium sulfate; solubilizers, such as ethanol or surface active agents and the like.

In the event that the adhesive properties of the sprayed enzyme solution and the introduced pulverulent support are not sufficient to ensure that the particles stick together in a stable manner after spraying, in addition the use of a binder is advantageous. This avoids the agglomerates disintegrating again on drying. In such cases it is preferred to spray into the fluidized bed a binder which is soluble or dispersible in an aqueous medium. The binder can be sprayed in either dissolved in the enzyme solution to be sprayed in, or separately therefrom, simultaneously or staggered in time. Examples of suitable binders are solutions of carbohydrates, for example glucose, sucrose, dextrins etc., sugar alcohols, for example mannitol, or polymer solutions, for example solutions of hydroxypropylmethylcellulose (HPMC), polyvinylpyrrolidone (PVP), ethoxylated cellulose (EC), ethylcellulose or propylcellulose. By specific choice of amount and adhesive properties of the binder sprayed in, agglomerates of different size and strength are formed.

If the binder is sprayed in a mixture with the enzyme, the binder content is usually in the range of from about 0.5 to 20% by weight, preferably from about 1 to 10% by weight, based on the total weight of the solution.

If the binder is sprayed as a separate solution, the binder content of the solution is in the range of from about 1 to 30%, based on the total weight of the solution. The binder in this case is also dissolved in an aqueous medium, preferably sterile, demineralized water. Customary additives, for example buffers or solubilizers, can also be present.

The content of the binder in the end product is according to the invention from 0 to about 20% by weight, for example from about 1 to 6% by weight. The optimum amount is also dependent on the type of binder selected. Care must be taken to avoid adverse effects on the product, for example its solution properties, clarity of the solution after dissolving the instant powder.

The invention also relates to the instant enzyme formulations obtainable using the above-described processes.

The invention relates in particular to instant enzyme formulations which comprise an agglomerated pulverulent material that is selected from
  i) an inorganic or organic support which is soluble or dispersible, preferably soluble, in aqueous medium;
  ii) an enzyme preparation which is soluble in aqueous medium; and
  iii) mixtures of i) and ii).

This pulverulent material has been agglomerated using an agglomerating medium, preferably an enzyme, a binder or an enzyme-binder mixture.

Preferably, instant enzyme formulations are prepared whose agglomerate particles have a mean particle size of greater than 0.45 mm, in particular up to about 8 mm. Preferably, the particle size is in the range of from about 0.5 to 6 mm, in particular from 0.8 to 3 mm.

The formulations of the invention are preferably also distinguished by a relatively high protein content, based on the total weight of the formulation. This is for instance in the range of from about 50 to 95% by weight, based on the total weight of the finished product. In addition, the formulations of the invention have a high content of enzymatically active protein.

The instant formulations of the invention comprise at least one enzyme which is selected from oxidoreductases, transferases, lyases, isomerases, ligases and hydrolases. Examples of hydrolases, i.e. enzymes which hydrolytically cleave chemical bonds, are esterases, glycosidases, ether hydrolases, proteases, amidases, aminidases, nitrilases and phosphatases. Glycosidases include both endoglucosidases and exoglucosidases which cleave both α- and β-glycosidic bonds. Typical examples of these are amylases, maltases, cellulases, endoxylanases, β-glucanases, mannanases, lysozymes, galactosidases, β-glucuronidases and the like. Preference is given in particular to non-starch-polysaccharide-cleaving enzymes, such as amylase, glucanase and xylanase, and to phosphatases, in particular phytase. Particularly preferred instant enzyme formulations comprise from $1\times10^4$ to $1\times10^5$ U of phytase per gram of total weight of formulation. 1 U of phytase is defined as the release of 1 micromole of inorganic phosphate per minute from an excess of phytate.

Depending on the mode of operation of the preparation process of the invention, the instant formulations are made up differently. Some typical structures may be mentioned as examples:

Agglomerate of particles of an inorganic or organic support, agglomerated with at least one enzyme, with or without an outer coating.

Agglomerate of particles of an inorganic or organic support, agglomerated with at least one enzyme/binder mixture, with or without an outer coating.

Agglomerate of particles of a dry enzyme preparation, agglomerated with at least one identical or different enzyme, with or without an outer coating.

Agglomerate of particles of a dry enzyme preparation, agglomerated with a mixture of at least one binder and at least one identical or different enzyme, with or without an outer coating.

Agglomerate of particles of a dry enzyme preparation, agglomerated with at least one binder, with or without an outer coating.

If desired, in the dry products of the invention, other constituents may be present, such as nutrient-relative additives, for example vitamins, amino acids, trace elements or preservatives.

The invention also relates to instant enzyme formulations of the above-described type, packaged in portions in soluble film pouches. The portion size can be chosen freely in principle, but is generally in the range of from about 100 g to 2000 g. The water-soluble films usable for portioning are known in the prior art and are freely available commercially. Preferably, polyvinylalcohol films are used, which are marketed in various quality grades, for example under the trade names Hydrosol® or Solublon®. The dissolution time for films of this type is in the order of magnitude of about 3 minutes. The film thickness depends on the portion size. A 30 μm film can be used, for example, for packaging a 500 g portion. One or more film pouches can expediently be provided with an aluminum-laminated outer package in order to keep moisture away from the film.

The invention further relates to feedstuff compositions which, in addition to conventional feed constituents, comprise at least one instant enzyme formulation of the invention as an admixture. The invention also relates to a feedstuff composition onto which has been applied at least one of the above-described instant enzyme formulations after dissolution or dispersion in an aqueous phase.

The present invention also relates to the use of instant enzyme formulations of the invention as feed additive.

The present invention is now described in more detail with reference to the following non-restricting examples and the accompanying figures.

Figure 1:
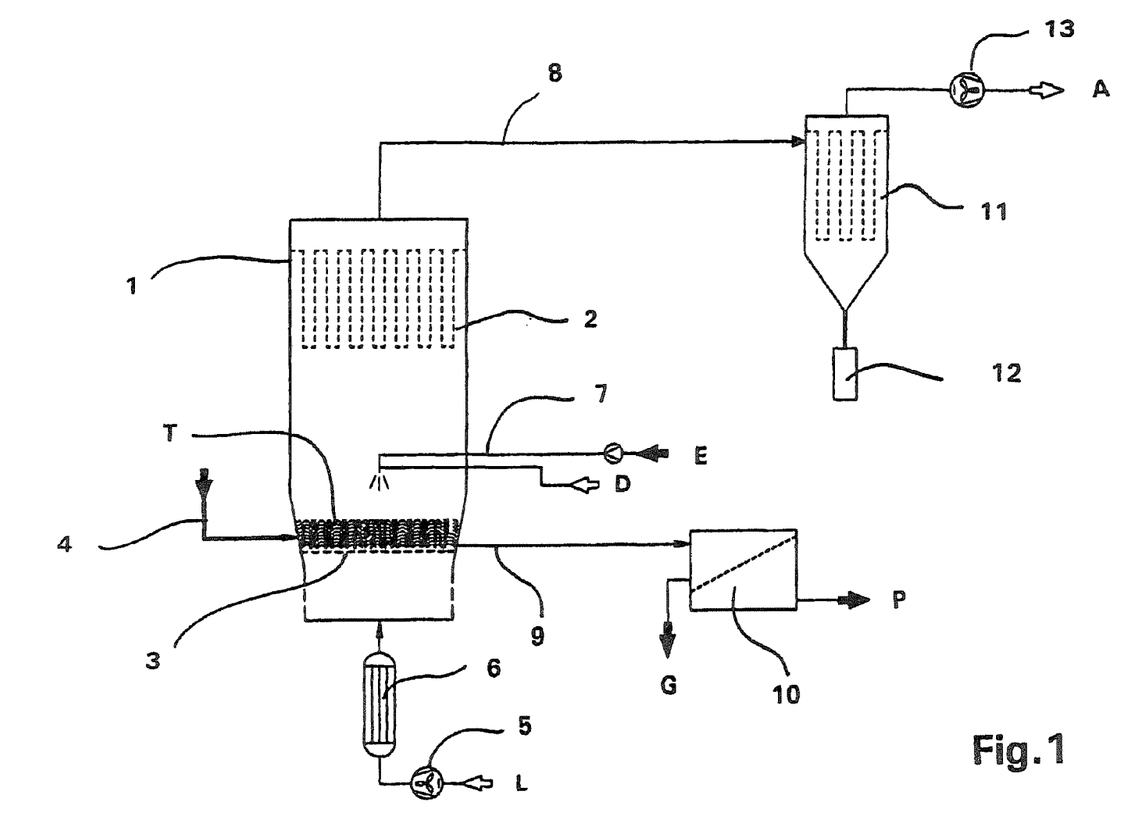
FIG. 1 diagrammatically shows a fluidized-bed dryer system for the batchwise preparation of a supported instant enzyme powder.

FIG. 1 diagrammatically shows a fluidized-bed dryer system for the batchwise preparation of a supported instant enzyme powder. Air L, which has been preheated by the heater 6, is introduced from the bottom using the fan 5 into a fluidized-bed dryer 1 which is provided with an internal filter 2 and a perforated plate 3. Via the product feed 4, a charge of support material T is introduced at the beginning of the process into the fluidized-bed dryer 1 and fluidized by the preheated air. Into the fluidized-bed dryer, above the fluidized bed, there is sprayed onto the fluidized bed thus formed enzyme solution E, with or without admixed binder, via the spray apparatus 7 using compressed air D. As soon as the desired amount has been sprayed in, the feed of enzyme solution E is interrupted, the crude agglomerate is if necessary post-dried in the fluidized bed and passed via the product discharge 9 out of the fluidized-bed dryer 1 into the screen apparatus 10, where it is separated into coarse material G and product P having the desired particle size. The process exhaust air A, after passing through the internal filter 2, is passed via the exhaust line A to the exhaust air filter 11, freed there from very fine particles which are collected in the container 12, and is removed from the system via the fan 13.

Figure 2:
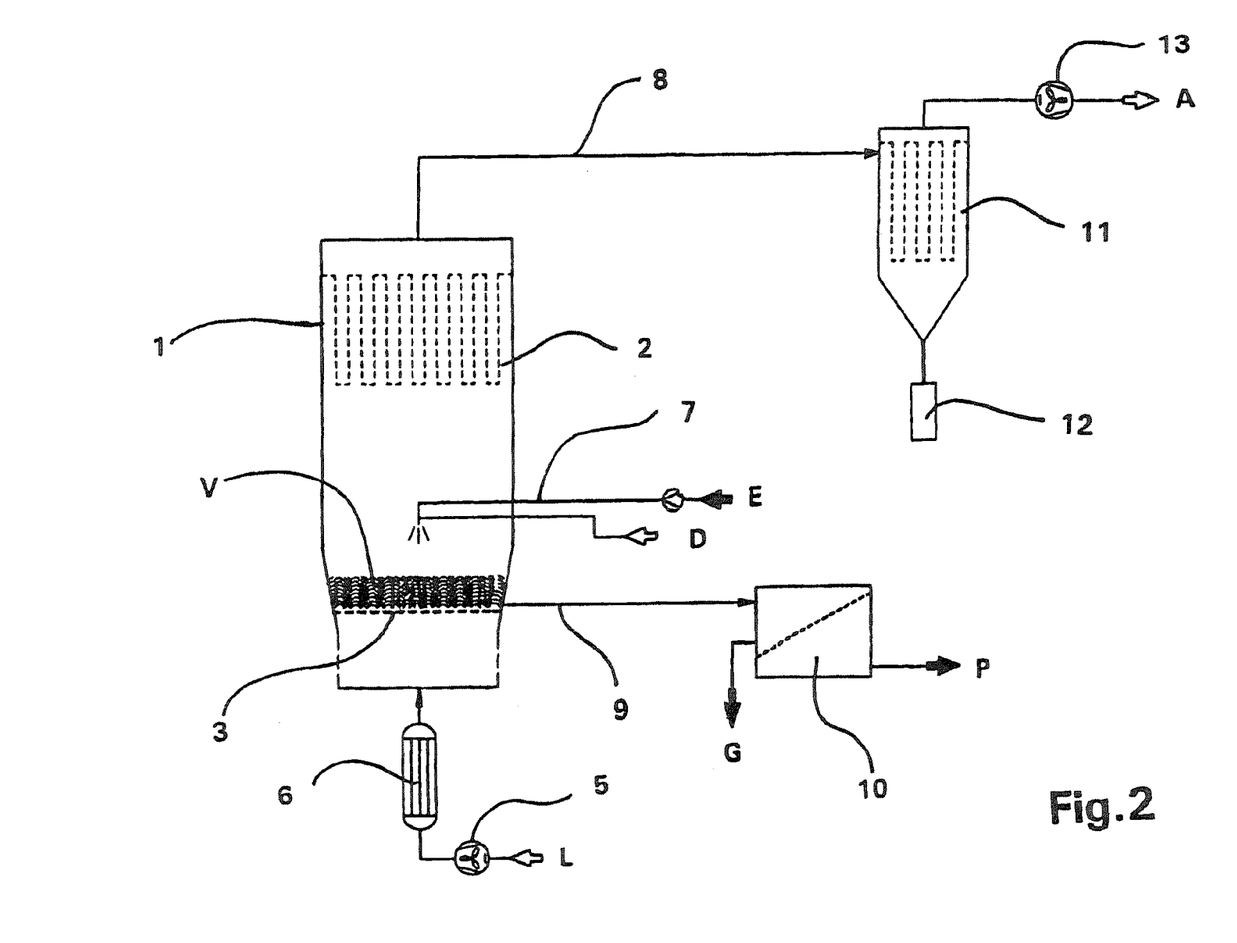
FIG. 2 shows a modification of the fluidized-bed system according to FIG. 1, which is designed for continuous operation.

FIG. 2 shows a modification of the fluidized-bed system according to FIG. 1, which is designed for continuous operation. In contrast to the apparatus according to FIG. 1, in the fluidized-bed dryer 1 support material V is introduced at the beginning of the continuous preparation process. Here, this is preferably a previously dried enzyme powder, which is subsequently fluidized, as described in FIG. 1, by blowing in preheated air, and sprayed and agglomerated with enzyme solution E. In contrast to the procedure shown in FIG. 1, here the agglomerate formed is not discharged via the exhaust line 9 batchwise, but is continuously discharged in correspondence with the amount of enzyme sprayed in and is worked up in the screen 10 as described above.

Figure 3:
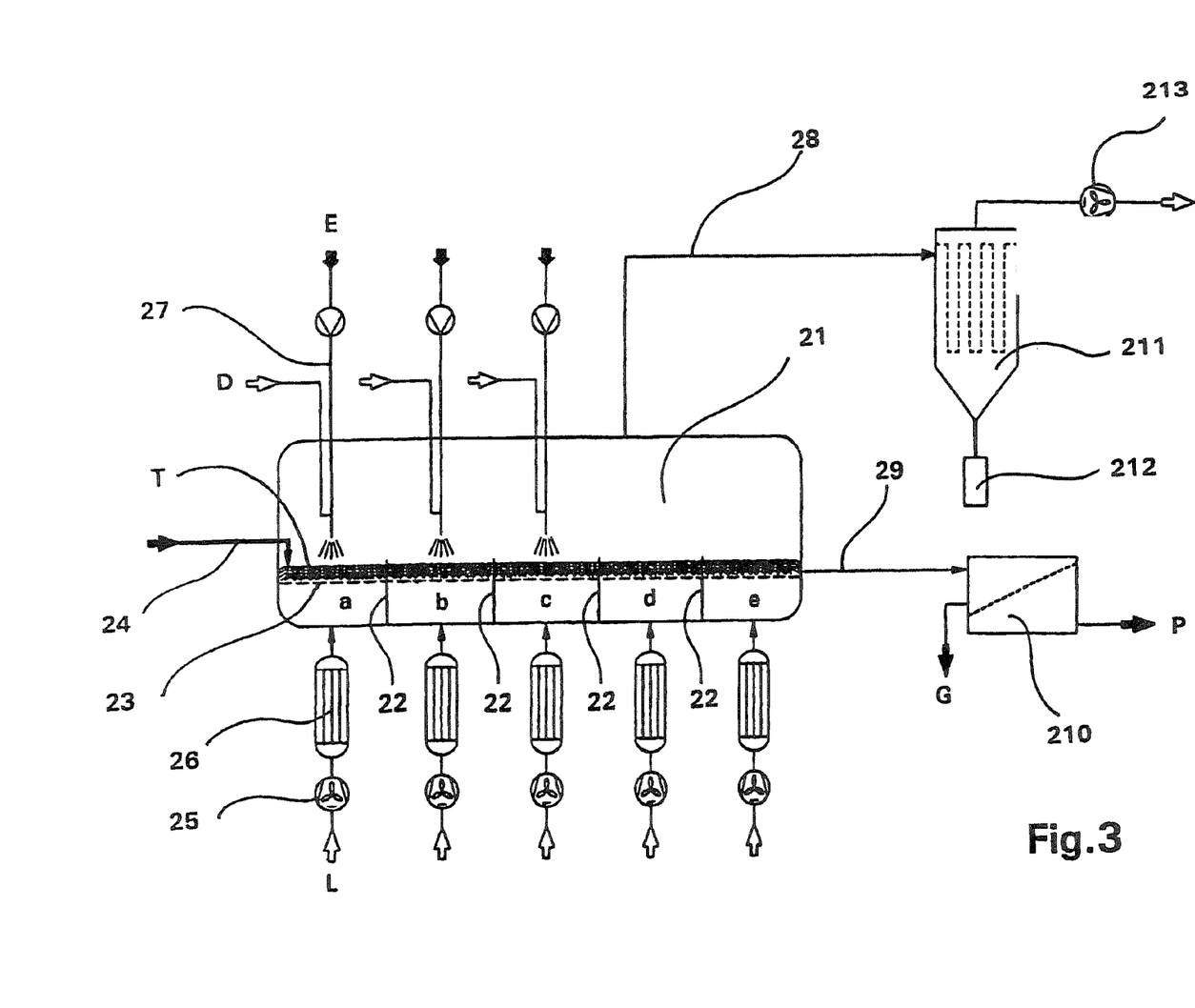
FIG. 3 shows a multistage fluidized-bed system for the continuous preparation of an instant powder of the invention.

FIG. 3 shows a multistage fluidized-bed system for the continuous preparation of an instant powder of the invention. The fluidized-bed dryer 21, equipped with a perforated sheet 23, is divided in its base area into the zones a, b, c, d and e using vertical partitions 22 which project above the top of the base. Three identical spray apparatuses 27 are assigned to the spray zones a, b and c, which spray apparatuses extend from the top into the fluidized-bed dryer and via which enzyme solutions E of identical or different composition are sprayed in using compressed air D. The spray zones are followed by the drying zones d and e. The zones a, b, c, d and e are designed to be open at the top, partitions projecting above the perforated plate 23 defining the individual zones of the fluidized bed. The partitions can be designed as overflow or underflow weirs. Support material T, which can be either an inorganic or organic powder or a spray-dried enzyme powder, is fed via the feed line 24 into the zone a and there fluidized.

It is fluidized using air L, which is taken in via a fan 25, preheated in the heater 26 and passed into the zone a from the bottom. As a result of spraying the enzyme solution E, agglomeration proceeds in the zone a: Likewise, enzyme solution E is sprayed into the zones b and c. The fluidization is performed in these zones using appropriately preheated air, further agglomeration also being carried out here. A part of the water, as in zone a also, is taken off by the heated air. The zones d and e are designed as pure drying zones. The finished agglomerate is discharged from zone e via the exhaust line 29 and is separated using the screen 210 into coarse material G and product P having the desired particle size. Exhaust air A is passed out of the dryer 21 via the line 28, freed from fine particles in the exhaust air filter 211 and removed from the process via the fan 213. The fine particles separated off are collected in the container 212.

Figure 4:
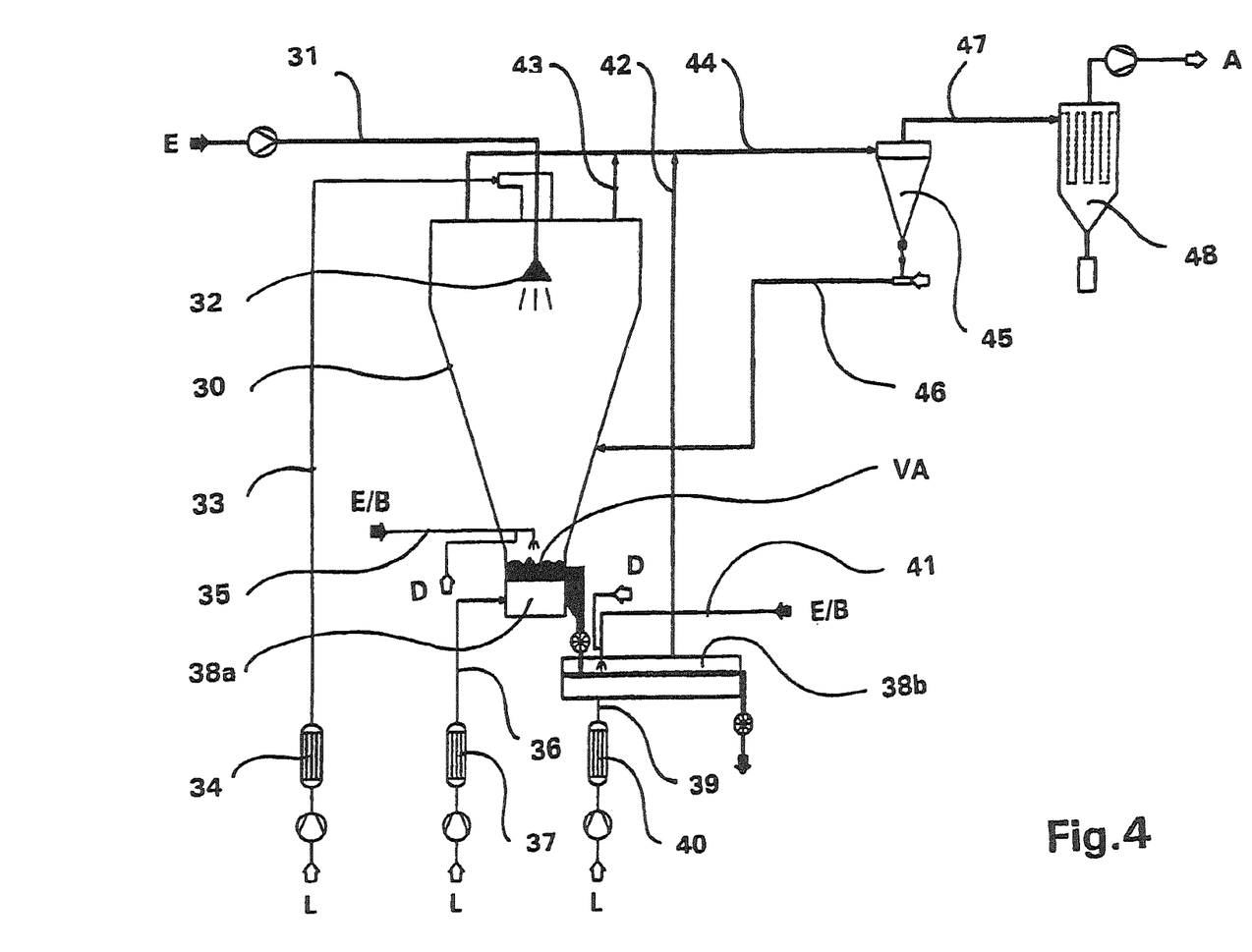
FIG. 4 shows a diagrammatic representation of a fluidized spray dryer (FSD) drying system for continuously preparing an instant enzyme powder of the invention.

FIG. 4 shows a diagrammatic representation of a fluidized spray dryer (FSD) drying system for continuously preparing an instant enzyme powder of the invention. In this case enzyme solution E is introduced via the feed line 31 into the top of the FSD dryer 30 and atomized using the atomizer 32. The drying is performed by introducing air in concurrent flow via the piping system 33. The air is preheated in this case via the heater 34. The spray-dried enzyme powder collects in the integrated fluidized bed 38a in the bottom of the FSD dryer 30 and is there sprayed with enzyme solution E and/or binder B using a spray apparatus 35, using compressed air D, and fluidized with introduced air. The air for this purpose is preheated using the heater 37 and fed via the feed line 36 beneath the gas distributor plate of the integrated fluidized bed 38a. The resultant preagglomerate VA then passes into a downstream external fluidized bed 38b. Into the fluidized bed 38b is introduced from the bottom via the feed line 39 air which has previously been preheated via the heater 40. The preagglomerate VA which is introduced in the fluidized bed is again sprayed with enzyme solution E and/or binder B using the spray apparatus 41, using compressed air D, and agglomerated to form the end product. The finished agglomerate is discharged from the fluidized bed and can, as described above, be further worked up (not shown). Exhaust air from the fluidized bed 38b and the FSD dryer 30 is passed via the piping system 42, 43, 44 to the cyclone 45 and there separated from fine material, which is recycled via the line 46 into the dryer 30. The prepurified exhaust air is removed from the process via the line 47 after passing through the filter 48.

The instant products of the invention prepared using apparatuses according to FIGS. 1 to 4 can be provided with an additional outer coating in a further process step. The apparatus which can be used for this is virtually identical to the batchwise system shown in FIG. 1. Instead of carrier material T, for this purpose enzyme agglomerate is introduced into the fluidized-bed dryer 1, fluidized using preheated air and simultaneously heated. Instead of enzyme solution E, a coating solution is sprayed on via the spray apparatus 7. The agglomerate thus coated is, with or without post-drying and cooling, removed from the fluidized-bed dryer 1 and freed from coarse material G in the screen 10. The process exhaust air is worked up as described in FIG. 1.

Example 1

Agglomeration in the fluidized bed with an introduced inorganic support (batch procedure).

The support (800 g) used was a screen fraction of sodium sulfate (<150 μm anhydrous). 20% of $MgSO_4.7H_2O$ were dissolved in the enzyme solution (phytase; dry matter 25.2%; 15,500 U/g). The support was introduced into the fluidized bed and the enzyme solution (7900 g) was sprayed on until the desired final activity and agglomerate size were achieved.

A laboratory fluidized bed from Niro-Aeromatic, type MP-1, having a large Plexiglass cone (gas distributor plate diameter 170 mm) and a perforated plate having 16% free area was used in the experiment.

Spraying was begun using a 1.2 mm two-component nozzle which, at the beginning, was installed at the bottom position of the cone and later, with a higher fluidized bed, was installed at the upper position of the cone (top-spray procedure). The solution was added using a diaphragm pump from ProMinent.

The spraying was continued for approximately 4 h, and then post-drying was performed for approximately 1 h. The feed air temperature was controlled as a function of the product temperature, which was 45° C. at the beginning and 40° C. after approximately 1 h. The feed air temperature which varied as a function of the preset product temperature, air flow rate and spraying rate, was from 52 to 56° C. during the first hour, then 50° C., slowly increasing to 65° C. by the end of spraying. During the post-drying, the feed air temperature fell back to 42° C. The air flow rate was 40 $m^3/h$ at the beginning, and was then increased stepwise to 120 $m^3/h$ by the end of spraying. During the post-drying a flow rate of 80 $m^3/h$ was operated. The spraying rate at the beginning was approximately 230 g/h, then it was increased stepwise to approximately 3500 g/h by the end of spraying. At the beginning the spraying pressure was 1.2 bar, then this was increased stepwise to 1.8 bar by 2 h of spraying time.

The agglomeration began after approximately 1.5 h and agglomeration became increasingly intense with further spraying time. The product discharge was coarse and relatively uniformly agglomerated and contained no fines fraction. 3700 g of product having a residual moisture content of 10% were discharged.

An instant powder having the following characteristics is obtained:
Residual moisture: from 6 to 12%
Activity: from 22,000 to 25,000 U/g (even higher with high-activity enzyme solutions (phytase)
Dust behavior: virtually dust-free by eye
Flow behavior: free-flowing by eye
Appearance: course, uniform and brown agglomerate, occasionally having some small lumps with can be screened out
Mean particle diameter: 1900 μm

Example 2

Agglomeration of an enzyme powder in the fluidized bed with binder (batch procedure)

Compared with the process according to Example 1, instead of the inert support material, a phytase powder (600 g; 33,000 U/g, residual moisture content 14%; if necessary finely agglomerated) was used as introduced material in the fluidized bed. The enzyme powder was a dry powder which was obtained by spray-drying. The spray solution used was a phytase solution (600 g; dry matter 25.2%; 15,500 U/g of activity). After spraying the phytase solution onto the introduced phytase powder, an HPMC solution (17 g of HPMC in 153 g of demineralized water) was immediately sprayed as binder onto the batch agglomerated under moist conditions and the enzyme powder was further agglomerated.

In the experiment, a laboratory fluidized bed from Niro-Aeromatic, type MP-1, having a large Plexiglass cone (gas distributor plate diameter 170 mm) and a perforated plate having 12% free area was used. Spraying was performed using a 1.0 mm two-component nozzle which was installed at the cone in the lower position (top spray procedure). The solutions were added using a diaphragm pump from ProMinent.

The enzyme-containing spray solution was sprayed for 30 min (spraying rate approximately 1500 g/h) and the binder-containing spray solution for 26 min (spraying rate approximately 1700 g/h). Post-drying was then performed for 30 min and cooling for 26 min. The feed air temperature was controlled according to the product temperature with a preset value of 40° C. The feed air temperature, which varied according to air flow rate and spraying rate, was from 80 to 85° C. during the spraying. During the post-drying, the feed air temperature was decreased to 41° C. The air flow rate was 25 m³/h at the beginning, and was then increased stepwise, corresponding to the increase in particle size, to 70 m³/h by the end of spraying and was 25 m³/h during post-drying and cooling. The spray pressure was 2.5 bar.

The enzyme powder was slightly agglomerated at the end of spraying the enzyme solution and was then further agglomerated by spraying on the binder solution. The binder additionally stabilized the agglomerates, so that these were retained after drying. Under the microscope, the agglomerates appeared firmly stuck together and uniform. 840 g of product having a residual moisture content of 9% were discharged.

In the process, an instant powder having the following characteristics is obtained:
Residual moisture: from 6 to 13%
Activity: from 30,000 to 35,000 U/g (even higher with high-activity enzyme solutions)
Dust behavior: virtually dust-free by eye
Flow behavior: free-flowing by eye
Appearance: coarse, uniform and brown agglomerate, occasionally having some small lumps with can be screened out
Mean particle diameter: 700 µm Example 3

Coating an instant powder in the fluidized bed (batch procedure)

Onto the instant powder (1500 g) obtained in accordance with Example 1, lumps had been screened out in advance, was sprayed a 20% strength Lutrol F68 solution (395 g; polyoxyethylene/polyoxypropylene block polymer). The end product has a coating content of approximately 5%. The coating was carried out in the same apparatus having the same setup as in Example 1. The two-component nozzle was installed on the cone in the lower position. The spraying time was approximately 45 min, and post-drying was then carried out for approximately 55 min. The feed air temperature was controlled as a function of the product temperature with a preset value of 40° C. The feed air temperature, depending on air flow rate and spraying rate, was from 45 to 50° C. During the post-drying, the feed air temperature fell to 40° C. The air flow rate was from 80 to 100 m³/h at the beginning During post-drying, the air flow rate was 80 m³/h. The spraying rate was approximately 530 g/h and the spraying pressure was 1.5 bar.

The product had a coarse and uniform appearance, was somewhat further agglomerated again by the spraying and contained few lumps. Under the microscope a smooth and closed coating layer could be seen. 1544 g of product having a residual moisture content of approximately 8% were discharged.

Example 4

Tests for Assessing the Instant Properties

To test the solution properties, a test was developed which is to simulate the handleability of the product at the client's premises.

For this purpose, 1960 g of water were introduced into a 3 liter glass beaker and were agitated at from approximately 220 to 240 rpm using an intensive stirrer. 40 g of the instant powder were then mixed in rapidly (from approximately 1 to 2 seconds). The batch corresponds to a 2% strength solution and, in the case of phytase, to an activity of from 400 to 600 U/g when an instant powder having an activity of from about 20,000 to 30,000 U/g is used. If the activity of the instant powder is outside the usual limits, the batch must be calculated for the corresponding activity. (Preset activity of the solution in the case of phytase—500 U/g). When the powder is added, a stopclock is started at the same time.

In the assessment of the instant properties, attention is paid particularly to the following points:
lump formation when the instant powder is added
timepoint of disintegration of the agglomerates
timepoint at which the powder is virtually completely dissolved (only a few large particles may still be present)
timepoint at which the powder is completely dissolved
foam formation during dissolution
clarity of the solution
other observations If the instant powder prepared in accordance with Example 1 is subjected to this test, the following profile results:
no lump formation on addition of the instant powder or during 10 the dissolution process;
the agglomerates disintegrate after approximately 30 seconds;
the instant powder is dissolved, apart from a few small particles, after approximately 1.5 minutes;
after in total 2.5 minutes even the last particles are dissolved;
no occurrence of foam;
after complete dissolution, the solution shows no turbidity.

We claim:

1. An instant enzyme formulation suitable for use in preparing feedstuff compositions comprising an agglomerate of pulverulent material, which pulverulent material has a mean particle size in the range of 30 to 300 µm, and which pulverulent material being selected from
   i) an enzyme preparation which is soluble in an aqueous medium, obtained by spray-drying an enzyme solution having a protein content of 1-50% by weight, optionally containing a buffer, an enzyme stabilizer selected from alkali metal or alkaline metal salts, a solubilizer, and/or a surface active agent; or
   ii) a mixture of i) and an inorganic or organic support suitable for use in a feedstuff composition which is soluble in an aqueous medium, wherein said inorganic or organic support is selected from sodium chloride, calcium carbonate, sodium sulfate, magnesium sulfate, glucose, fructose, or sucrose;
the agglomerate having a protein content of about 50-95% by weight of the formulation, and wherein its agglomerated particles have a mean particle size of between about 0.45 mm and about 8 mm and is water soluble.

2. The instant enzyme formulation of claim 1, wherein the agglomerated particles have a mean particle size between about 0.45 mm and about 3mm.

3. The instant enzyme formulation of claim 1, wherein the agglomerated particles are additionally provided with a water-soluble coating.

4. The instant enzyme formulation of claim 1 packaged in portions in water-soluble film pouches.

5. A pelletized feedstuff composition comprising pellets containing conventional feed constituents, wherein the instant enzyme formulation of claim 1 in dissolved form is applied onto the feed pellets.

6. The instant enzyme formulation of claim 1, further comprising a binder.

7. The instant enzyme formulation of claim 6, wherein the binder is selected from the group consisting of
 (a) a low molecular organic binder comprising a solution of a carbohydrate and a sugar alcohol;
 (b) a binder comprising a polymer solution; and
 (c) a polymeric binder comprising a solution of hydroxypropylmethylcellulose, polyvinylpyrrolidone, ethoxylated cellulose, ethylcellulose, or propylcellulose.

8. The instant enzyme formulation of claim 1 comprises an inorganic support, wherein the inorganic support is sodium chloride, calcium carbonate, sodium sulfate or magnesium sulfate.

9. The instant enzyme formulation of claim 1 comprises an organic support, wherein the organic support is glucose, fructose or sucrose.

10. The instant enzyme formulation of claim 1, wherein the inorganic or organic support has a particle size in the range of 30 to 300 μm.

11. The instant enzyme formulation of claim 1, wherein the enzyme is selected from oxidoreductases, transferases, lyases, isomerases, ligases, phosphatases, or hydrolases.

12. The instant enzyme formulation of claim 11, wherein the phosphatase is phytase.

13. The instant enzyme formulation of claim 11, wherein the hydrolase is a non-starch-polysaccharide-cleaving enzyme.

14. The instant enzyme formulation of claim 1, wherein the instant enzyme formulation when dissolved in a 2% solution in water by stirring results in at least the instant properties comprising
 (a) no lump formation on addition of the powder to water or during the dissolution process;
 (b) complete dissolution after 2.5 minutes; and
 (c) no turbidity of the solution after complete dissolution.

15. A process for preparing an instant enzyme formulation suitable for use in preparing feedstuff compositions, which comprises:
 (a) making a pulverulent material by the method selected from:
  i) an enzyme preparation which is soluble in an aqueous medium made by spray-drying an enzyme solution having a protein content of 1-50% by weight, optionally containing a buffer, an enzyme stabilizer selected from alkali metal or alkaline metal salts, a solubilizer, and/or a surface active agent; or
  ii) applying a mixture of i) with an inorganic or organic support suitable for use in a feedstuff composition which is soluble in an aqueous medium, wherein said inorganic or organic support is selected from sodium chloride, calcium carbonate, sodium sulfate, magnesium sulfate, glucose, fructose, or sucrose;
 wherein the pulverulent material has a mean particle size in the range of 30 to 300 μm and
 (b) agglomerating the pulverulent material by simultaneous or time-staggered spraying of one or more spray media to form an instant powder, the spray media being selected from enzyme solutions, binder solutions, binder dispersions, or binder and enzyme solutions, wherein the binder is soluble in an aqueous solution; wherein agglomeration is carried out to a mean particle size between about 0.45 mm and about 8 mm; and wherein the particles have a protein content of about 50 to 95% by weight of the formulation
 wherein the agglomerate is water soluble.

16. The process of claim 15, wherein the agglomeration is carried out continuously or batchwise in a fluidized bed.

17. The process of claim 15, wherein agglomeration is carried out to a mean particle size between about 0.45 mm and about 3 mm.

18. The process of claim 15, wherein the agglomeration is carried out using a fluidized bed which is internally integrated into the spray-dryer or using an external fluidized bed.

19. The process of claim 15, wherein the agglomerate is dried to a residual moisture content of less than about 15% by weight.

20. The process of claim 15, wherein the agglomerate particles are provided with a water-soluble coating and then if necessary are dried again.

21. The process of claim 15, wherein the binder is selected from the group consisting of
 (a) a low molecular organic binder comprising a solution of a carbohydrate and a sugar alcohol;
 (b) a binder comprising a polymer solution; and
 (c) a polymeric binder comprising a solution of hydroxypropylmethylcellulose, polyvinylpyrrolidone, ethoxylated cellulose, ethylcellulose, or propylcellulose.

22. The process of claim 15 is carried out with an inorganic support, wherein the inorganic support is sodium chloride, calcium carbonate, sodium sulfate or magnesium sulfate.

23. The process of claim 15 is carried out with an organic support, wherein the organic support is glucose, fructose or sucrose.

24. The process of claim 15, wherein the inorganic or organic support has a particle size in the range of 30 to 300 μm.

25. The process of claim 15, wherein the enzyme is selected from oxidoreductases, transferases, lyases, isomerases, ligases, phosphatases, or hydrolases.

26. The process of claim 25, wherein the phosphatase is phytase.

27. The process of claim 25, wherein the hydrolase is a non-starch-polysaccharide-cleaving enzyme.

28. The process of claim 15, wherein the instant enzyme formulation when prepared in a 2% solution in water by stirring results in at least the instant properties comprising
 (a) no lump formation on addition of the powder to water or during the dissolution process;
 (b) complete dissolution after 2.5 minutes; and
 (c) no turbidity of the solution after complete dissolution.

29. A process for preparing a pelletized feedstuff composition supplemented with enzyme comprising
 1) preparing feedstuff pellets and
 2) applying onto the pellets a solution of an instant enzyme formulation prepared by the method of claim 15.

30. The process of claim 29, wherein the agglomeration is carried out continuously or batchwise in a fluidized bed.

31. The process of claim 29, wherein agglomeration is carried out up to a mean particle size between about 0.45 mm and about 3 mm.

32. The process of claim 29, wherein the agglomeration is carried out using a fluidized bed which is internally integrated into the spray-dryer or using an external fluidized bed.

33. The process of claim 29, wherein the agglomerate is dried to a residual moisture content of less than about 15% by weight.

34. The process of claim 29, wherein the agglomerate particles are provided with a water-soluble coating and then if necessary are dried again.

35. The process of claim 29, wherein the enzyme is selected from oxidoreductases, transferases, lyases, isomerases, ligases, phosphatases, or hydrolases.

36. The process of claim 35, wherein the hydrolase is a non-starch-polysaccharide-cleaving enzyme.

37. The process of claim 35, wherein the phosphatase is phytase.

38. The process of claim 29, wherein the instant enzyme formulation to be applied onto the feedstuff pellets comprises from $1\times10^4$ to $1\times10^5$ U of phytase per gram of total weight of the formulation.

39. The process of claim 29, wherein the instant enzyme formulation is packaged in portions in water-soluble film pouches.

40. The process as claimed in claim 29, wherein the inorganic or organic support has a particle size in the range of 30 to 300 µm.

41. The process of claim 29, wherein the instant enzyme formulation when dissolved in a 2% solution in water by stirring results in at least the instant properties comprising
 (a) no lump formation on addition of the powder to water or during the dissolution process;
 (b) complete dissolution after 2.5 minutes; and
 (c) no turbidity of the solution after complete dissolution.

* * * * *